(12) United States Patent
Jofre Araya

(10) Patent No.: US 9,895,208 B2
(45) Date of Patent: Feb. 20, 2018

(54) PROSTHETIC RETENTION SYSTEM FOR EDENTULOUS PATIENTS CONSISTING OF A PREFABRICATED BAR AND TWO IMPLANTS

(75) Inventor: Jorge Antonio Jofre Araya, Concepcion (CL)

(73) Assignee: UNIVERSIDAD DE CONCEPCION, Concepcion (CL)

(*) Notice: Subject to any disclaimer, the term of this patent is extended or adjusted under 35 U.S.C. 154(b) by 0 days.

(21) Appl. No.: 14/369,430

(22) PCT Filed: Sep. 13, 2012

(86) PCT No.: PCT/CL2012/000053
§ 371 (c)(1),
(2), (4) Date: Jun. 27, 2014

(87) PCT Pub. No.: WO2013/097044
PCT Pub. Date: Jul. 4, 2013

(65) Prior Publication Data
US 2014/0349252 A1     Nov. 27, 2014

(30) Foreign Application Priority Data
Dec. 28, 2011 (CL) .................................. 3323-2011

(51) Int. Cl.
*A61C 8/00* (2006.01)
*A61C 1/08* (2006.01)

(52) U.S. Cl.
CPC ............ *A61C 8/0075* (2013.01); *A61C 1/084* (2013.01); *A61C 8/0048* (2013.01)

(58) Field of Classification Search
CPC ....... A61C 8/00; A61C 8/0075; A61C 8/0068; A61C 8/0022; A61C 8/027; A61C 1/084

USPC .................................. 433/172, 173, 174, 176
See application file for complete search history.

(56) References Cited

U.S. PATENT DOCUMENTS

| | | | |
|---|---|---|---|
| 4,877,400 A | 10/1989 | Holsclaw | |
| 7,377,781 B1 | 5/2008 | Karapetyan | |
| 7,699,611 B2* | 4/2010 | Feijtel | A61C 13/275 433/173 |
| 2008/0153063 A1* | 6/2008 | Mullaly | A61C 8/0018 433/174 |
| 2008/0241790 A1* | 10/2008 | Gittleman | A61C 8/0053 433/174 |
| 2010/0209874 A1 | 8/2010 | Auderset et al. | |
| 2011/0129799 A1 | 6/2011 | Kwan | |
| 2011/0195379 A1* | 8/2011 | Allaire | A61C 8/0048 433/174 |

(Continued)

FOREIGN PATENT DOCUMENTS

ES    2261645 T3    11/2006

OTHER PUBLICATIONS

International Search Report issued in PCT Application No. PCT/CL2012/000053.

*Primary Examiner* — Nicholas Lucchesi
(74) *Attorney, Agent, or Firm* — Lucas & Mercanti, LLP

(57) ABSTRACT

A prosthetic retention system for edentulous patients comprising a prefabricated bar and two implants; where the said bar consists of a tubular central piece that has a round or ovoid cross section and two hollow capsules at its ends; and where the implants are formed by one single piece, with an upper zone that connects to the bar and a lower zone that is introduced into the patient's bone tissue.

7 Claims, 3 Drawing Sheets

(56) References Cited

U.S. PATENT DOCUMENTS

2012/0189985 A1* 7/2012 Iglesias ............... A61C 8/0048
          433/174
2014/0134571 A1* 5/2014 Lemke ............... A61C 8/0095
          433/174

* cited by examiner

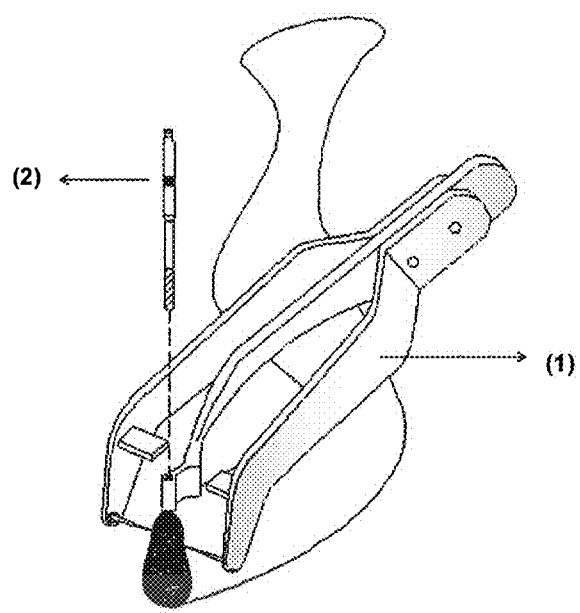
FIG.3.A
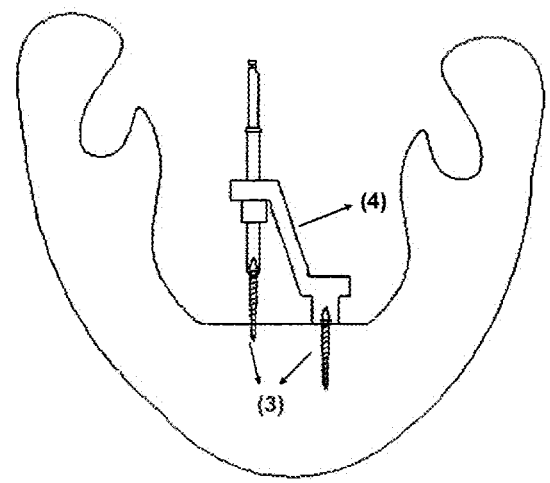
FIG.3.B

PROSTHETIC RETENTION SYSTEM FOR EDENTULOUS PATIENTS CONSISTING OF A PREFABRICATED BAR AND TWO IMPLANTS

CROSS REFERENCE TO RELATED APPLICATION

This Application is a 371 of PCT/CL2012/000053 filed on Sep. 13, 2012, which claims the priority of Chile Patent Application No. 3323-2011 filed on Dec. 28, 2011 both applications are incorporated herein by reference in their entirety.

TECHNICAL SECTOR

The technology, a prosthetic retention system for edentulous patients consisting of a prefabricated bar and two implants, is designed for use in dentistry.

PRIOR ART

At present, more than 30% of adults over 65 are completely edentulous, a situation that affects their self-esteem and quality of life. Osseointegrated implants have solved this problem to a certain degree, using a minimum of two mandibular implants. However, the high cost of these implants, and the complexity and the associated surgical trauma make routine use in public health systems difficult and reduce the effectiveness of rehabilitative treatment and the possibility of allocating funds to a large section of the population.

Edentulous adults are often treated with a small-diameter, low-cost and relatively simple implant that is available on the market. These implants have the advantage of being minimally invasive and of not requiring incisions or significant bone volume, thus avoiding surgical trauma. Unfortunately, these same factors produce the system's disadvantages. Because it is a "blind" surgical technique, without a flap, there is a greater risk of inserting the implant outside the bone tissue. In addition, the implant's reduced diameter seems to violate all known biomechanical principles for ensuring long-term integration of the implants into the bone tissue.

These evident risks and the absence of scientific evidence make it necessary to use conventional implants (>3.5 mm) despite the well-known problems of cost, complexity and patient trauma.

There are various prosthetic retention options when using mandibular implants. The one leading to the highest degree of stability over time and the lowest repair costs is an individually-designed metal bar which is screwed onto the implants. This system is used with conventional implants with a minimum diameter, enabling the screws to be inserted into threads on the inside of the implants. Small-diameter, minimally invasive implants cannot use this type of bar, as they do not have an internal screw system for fixation.

These bars must be produced in laboratories in a series of stages; they require a significant amount of time and technology and have an approximate cost of U.S. $500. Moreover, additional sessions with the patient are required to complete treatment, which can last from weeks to months.

The Swiss company CENDRES+MÉTAUX offers the prefabricated SFI-bar® that has a system of guide grooves and adjustable screws at its ends, enabling adaptation to the previously-inserted implants. This system is designed for immediate loading. In the case of conventional implants, however, the need for sutures and the possible damage to tissue during surgery, in addition to the impossibility of keeping the implants in a centered position and the large size of the bar and screws, make immediate clinical adjustment of the prostheses difficult, and additional laboratory stages are then required for prosthetic adjustment.

It is therefore necessary to develop technologies to solve these types of problems.

FIG. 3A shows the guide-forceps used to carry out the perforations for the implants.

FIG. 3B shows a telescopic insertion support used to insert the implants.

DESCRIPTION OF THE INVENTION

Figure 1:
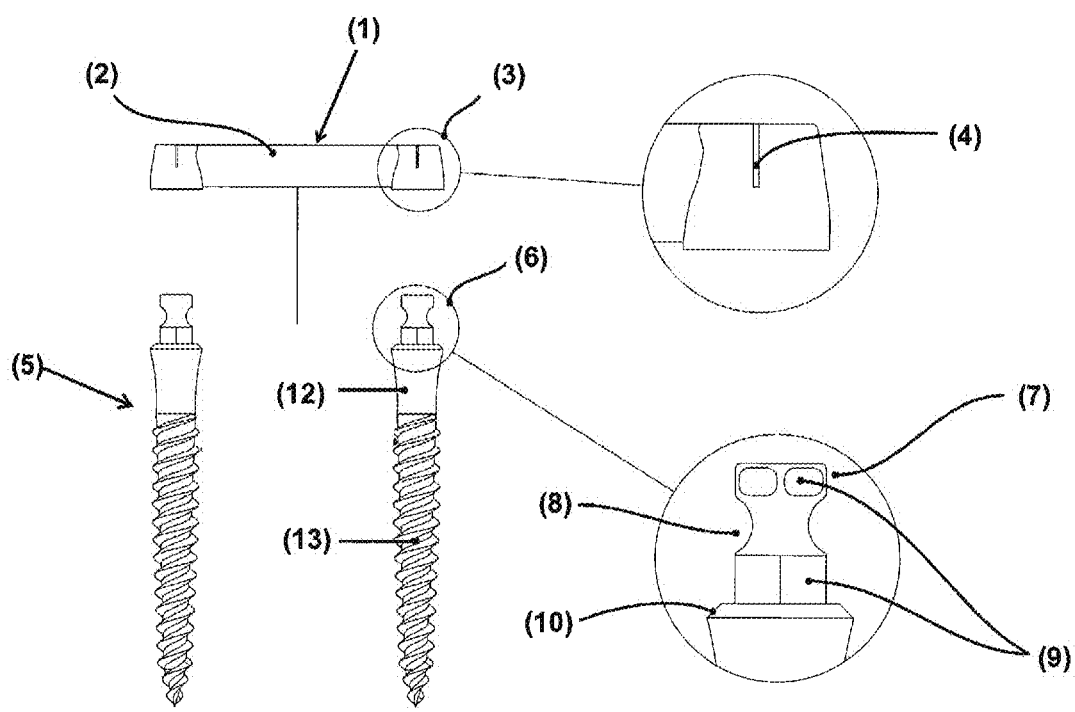
FIG. 1 shows the prosthetic retention system according to the invention.
Figure 2:
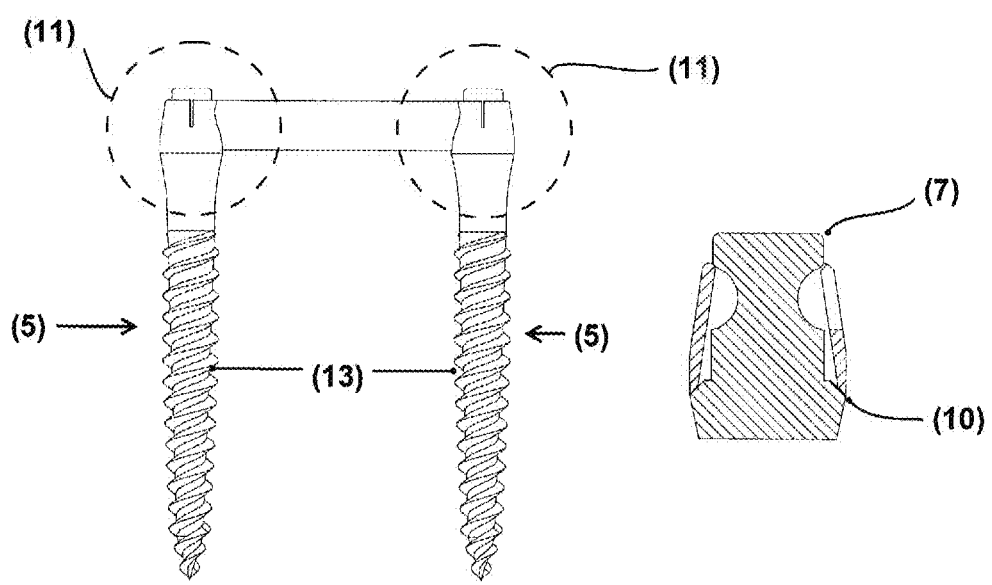
FIG. 2 shows the implants according to the invention.

The present technology consists of a prosthetic retention system for edentulous patients that comprises a prefabricated bar and two implants. FIGS. 1 and 2 will be used as a reference for a better understanding of the invention.

The bar (1) consists of a tubular central part (2) preferably made from a titanium alloy or surgical steel, which has a round or ovoid cross section of between 1 and 2 mm in diameter. At its ends it has two hollow capsules (3), with a distance of between 10 and 25 mm from center to center (ideally 11 mm), with a conical shape slightly larger than the implant heads, which can have a groove (4) on one or both sides. These grooves (4) take up a part or all of the side of the bar (1), leaving one or both sides partially or totally open for opening one end in case it is necessary to remove the bar and to facilitate flexibility in this zone during insertion.

The implants (5) are made from one piece, preferably from a TiAlV alloy that can be thermally treated for improved mechanical properties. The implants consist of an upper zone (6) referred to as the implant connection, formed by 2 hexagonal pieces (9) joined by a convex central part (8) enabling O-ring retention if the implant is used individually. The upper hexagonal part, corresponding to the implant head, has a contour of rounded angles (7), and the lower hexagonal part has flat faces matching those of the implant head and preventing rotation when inserting the implant. At the base of the upper zone there is a bezel (10) useful for adjusting the bar capsules (3).

The lower zone of the implants, corresponding to the part that is introduced into the tissue, has a smooth cylindrical-conical section of 1.5-4 mm in diameter that is in contact with the gums (12), and a rough section that is in contact with the bone tissue (13) formed by an elongated body of between 10 and 20 mm in length, with a cylindrical-conical shape of 1-2 mm in diameter, with a double thread that increases in width with distance from the implant point.

The system is completed when the bar (1) is inserted into the upper end (6) of the implants. The bar is inserted applying pressure and remains in place due to the larger diameter of the head (7) of the implants, adjusting to the bezel of the base (10) and thus creating a single system (11) that does not require cement or screws.

The head (7) of the implant enables capsule fixation (3), and the convex part connecting the hexagonal pieces can be used for O-ring retention if the implant is used individually without the bar.

For correct system operation, it is recommended that forceps be used to guide the positioning of the implants to ensure that they are parallel, at the same height, and centered on the bone.

The system does not require special screws for fixation, provides long-term stability optimizing clinical behavior after insertion, facilitates immediate loading, and does not require laboratory work. In addition, the bar (1) provides optimal prosthesis stabilization, reduces long-term prosthetic complications and associated costs, and can be removed if necessary without having to change the implants.

The benefits of this integrated system are:
minimal use of instruments and equipment for insertion;
simplicity, safety and precision, with a minimum number of components;
improved biomechanical properties due to the stabilization bar;
minimally invasive operation with minimal surgical risks;
immediate loading;
no incisions or convalescence required;
lower treatment costs; and
long-term clinical validation in a representative national sample consisting of public health patients.

Application Examples

In order to provide long-term treatment with reduced trauma, complexity and costs for edentulous patients, an integrated system was developed for stabilizing dental prostheses, comprising two implants and a prefabricated prosthetic bar. In addition, instruments such as a 3D positioning guide-forceps and a telescopic insertion support were used to facilitate insertion.

The surgical procedure used to verify the effectiveness of the technology is described below (see FIG. 3):

First, infiltration local anesthesia was applied and a guide-forceps (1) was used to measure the thickness of the osseous tissue in the implant area. This guide-forceps made it possible to carry out perforations for the implants in a minimally invasive fashion, without the need for a gum flap. Perforations were carried out with 1 mm drills (2) in the center of the mandible and in areas with a minimum bone thickness of 2 mm.

Then, the first implant (3) was inserted and the position of the forceps was changed, it being supported on the head of the implant, after which the second perforation was made. The telescopic insertion support (4) was subsequently introduced into the head of the first implant and the second implant (3) was inserted. The heads of both implants were adjusted to ensure that they were at the same height and at a distance of 11 mm from one another. The prosthetic bar was inserted onto the heads of the implants and remained locked into place.

After the prosthetic bar was installed, the pre-existing prosthesis of the patient was adapted and the retention clip was fixed by hollowing out the part of the prosthesis where the bar with the clip is fixed. Subsequently, the bar was covered with perforated rubber covering the gingiva, revealing the retention zones of the clip through the perforation and exposing the part of the clip to be fixed to the prosthesis. Finally, acrylic was applied to the hollowed zone of the prosthesis and placed on the rubber, so that the flaps of the clip were fixed to the prosthesis. In addition to providing prosthetic retention, the bar also improved the system's biomechanical properties, with clinical behavior equal to or better than conventional implants.

This procedure was validated in a randomized controlled clinical trial lasting 5 years in which 90 implants were inserted into 45 completely edentulous elderly patients being treated in the public health care system. Each patient received two implants in the anterior mandible through a procedure carried out without incisions that was completely guided to reduce surgical risks. Immediately after insertion, the bars were connected to retain the prosthesis to the patient's half. The other half was left with an O-ring retention system.

The degree of success of the bar system was 97.7%, higher than conventional implant systems with a documented success rate of 90%-95% after five years. The insertion procedure lasted approximately 2 hours.

The invention claimed is:

1. A prosthetic retention system for edentulous patients, which does not require the use of cement or screws, comprising:
   a bar and two implants,
   each implant comprises an upper zone, a lower zone and a cylindrical-conical section between the upper zone and the lower zone;
   the upper zone comprises an implant head, a base with a bezel and a convex zone between the implant head and the base;
   the lower zone corresponds to the part that is introduced into the patient's bone tissue;
   the bar comprises:
   a tubular central part having a round or ovoid cross section of 1-2 mm in diameter;
   a hollow capsule at each end of the bar, the hollow capsule having a conical shape slightly larger than an implant head and a groove which allows the bar to be inserted by applying pressure in the upper zone of the implants,
   wherein the bar has a predetermined nonadjustable fixed length;
   wherein the implants are adapted to be parallel to each other, at the same height and centered on the bone tissue; and
   wherein the hollow capsule at each end of the bar is separated by a fixed distance of 10-25 mm between their centers.

2. The prosthetic retention system for edentulous patients according to claim 1, wherein the grooves take up a part or all of the face of the bar, leaving one or both sides partially or totally open.

3. The prosthetic retention system for edentulous patients according to claim 1, wherein the bar is made from a titanium alloy or surgical steel.

4. The prosthetic retention system for edentulous patients according to claim 1, wherein the upper zone of each implant further comprises an upper hexagonal piece and a lower hexagonal piece joined by the convex zone, wherein the upper hexagonal piece corresponds to an implant head and has a contour of rounded angles, and wherein the lower hexagonal piece has flat faces that match the faces of an implant head.

5. The prosthetic retention system for edentulous patients according to claim 4, wherein each implant head locks with and fixes a capsule of the bar and wherein the convex zone that connects the upper hexagonal piece and the lower hexagonal piece retains an O-ring when an implant is used individually.

6. The prosthetic retention system for edentulous patients according to claim 1, wherein the capsules of the bar are separated by a fixed distance of 11 mm.

7. The prosthetic retention system for edentulous patients according to claim 1, wherein a guide-forceps is required to insert the two implants to keep them parallel to each other, at the same height and centered on the bone tissue of the patient.

* * * * *